United States Patent
Simoni et al.

(10) Patent No.: US 9,883,903 B1
(45) Date of Patent: Feb. 6, 2018

(54) SYSTEMS AND METHODS FOR ANALYZING AN ELECTROSURGICAL UNIT

(71) Applicant: LLOYD INDUSTRIES, INC., St. Charles, MO (US)

(72) Inventors: Lucio Simoni, St. Charles, MO (US); Aaron Littich, O'Fallon, MO (US)

(73) Assignee: LLOYD INDUSTRIES, INC., St. Charles, MO (US)

( * ) Notice: Subject to any disclaimer, the term of this patent is extended or adjusted under 35 U.S.C. 154(b) by 391 days.

(21) Appl. No.: 14/702,385

(22) Filed: May 1, 2015

(51) Int. Cl.
- A61B 18/00 (2006.01)
- A61B 18/12 (2006.01)
- A61B 19/00 (2006.01)

(52) U.S. Cl.
CPC ...... *A61B 18/1206* (2013.01); *A61B 19/5225* (2013.01); *A61B 2018/00642* (2013.01); *A61B 2018/00785* (2013.01); *A61B 2018/00898* (2013.01); *A61B 2560/0475* (2013.01); *A61B 2560/0487* (2013.01)

(58) Field of Classification Search
CPC .... A61B 17/07207; A61B 2017/07285; A61B 2017/00734; A61B 2017/0046; A61B 2017/00398; A61B 2017/00137; A61B 2017/00199; A61B 2017/00017; A61B 2017/00477; A61B 2017/2927; A61B 2017/07271; A61B 2017/00725; A61B 2017/00115; A61B 18/1445; A61B 18/1233; A61B 2018/00577; A61B 2018/00791; A61B 2018/00803; A61B 2018/162; A61B 2018/00821; A61B 2018/00648; A61B 2018/00702; A61B 2018/00797; A61B 2018/00815
See application file for complete search history.

(56) References Cited

U.S. PATENT DOCUMENTS

| 6,142,992 A | * | 11/2000 | Cheng | ............... | A61B 18/1206 |
| | | | | | 606/34 |
| 9,649,147 B2 | * | 5/2017 | Gilbert | ............... | A61B 18/1206 |
| 2015/0320479 A1 | * | 11/2015 | Cosman, Jr. | ....... | A61B 18/1482 |
| | | | | | 606/35 |

* cited by examiner

*Primary Examiner* — Brian T Gedeon
(74) *Attorney, Agent, or Firm* — Barta, Jones & Foley, P.C.

(57) ABSTRACT

Systems and methods for analyzing an electrosurgical unit are provided. One system includes an electrosurgical unit analyzer having an input configured to receive radio frequency (RF) signals from an electrosurgical generator and a measurement subsystem configured for programmable waveform detection corresponding to the received RF signals. The measurement subsystem includes a field-programmable gate array (FPGA) defining one or more thresholds for the waveform detection. The electrosurgical unit analyzer further includes a user interface displaying information relating to individual pulses detected from the RF signals.

17 Claims, 7 Drawing Sheets

SYSTEMS AND METHODS FOR ANALYZING AN ELECTROSURGICAL UNIT

BACKGROUND

Medical instruments may be used during a medical procedure to facilitate or assist in performing a particular operation. For example, electrosurgical devices may be used to heat tissue within a patient. The electrosurgical devices operate to apply a high-frequency electric current to the tissue. The use of electrosurgical devices allows for precise tissue cutting with reduced or limited blood loss. As such, electrosurgical devices are often used during surgical operations to help prevent blood loss in hospital operating rooms or in outpatient procedures.

Electrosurgery with electrosurgical devices is performed using an electrosurgical generator (commonly referred to as power supply or waveform generator) and a hand-piece including one or several electrodes, which is sometimes referred to as an RF Knife. For example, during cutting operation, the electrodes contact the tissue and a sufficiently high power density is applied to vaporize the water content of the tissue. Additionally, different waveforms may be used for different electrosurgical procedures, such as continuous single frequency waveforms or pulsed waveforms.

Testing of electrosurgical devices may be performed to ensure that the devices meet certain performance criteria, operate within specified or required guidelines and/or comply with different healthcare regulations. Electrosurgical analyzers are known and have been used to test electrosurgical devices, such as to measure the RF waveforms generated by the electrosurgical devices. For example, at least one known testing device includes thermal converters that use the RF signal to heat an element and have an output that is relative to the increase in temperature of the element. However, these testing devices only provide a root mean square (RMS) measurement from the current transformer. As more complex waveforms are used, including pulsed waveforms, these testing devices cannot be used to test the electrosurgical devices and analyze, for example, the pulsed waveforms, because the testing devices are not fast enough to respond to the pulsed waveform.

Other testing devices are known that use an integrated circuit (IC) that converts the RF waveform to an RMS DC voltage. The RMS voltage is DC and is measured by an Analog to Digital (A/D) converter. The DC voltage is proportional to the RMS of the input waveform. However, similar to the thermal test method, this technique is fairly slow to respond to the incoming waveform and cannot read pulsed waveforms properly.

Thus, conventional testing devices cannot provide the response time required for testing some waveforms, including more complex waveforms, and pulsed waveforms, and also do not provide digitization and sampling of the incoming waveform. Thus, a need exists for a testing device that can analyze these more complex waveforms, including pulsed waveforms.

SUMMARY

In one embodiment, an electrosurgical unit analyzer is provided that includes an input configured to receive radio frequency (RF) signals from an electrosurgical generator and a measurement subsystem configured for programmable waveform detection corresponding to the received RF signals. The measurement subsystem includes a field-programmable gate array (FPGA) defining one or more thresholds for the waveform detection. The electrosurgical unit analyzer further includes a user interface displaying information relating to individual pulses detected from the RF signals.

In another embodiment, a method for analyzing radio frequency (RF) signals from an electrosurgical generator is provided. The method includes acquiring as an input, RF signal from the electrosurgical generator and performing waveform detection on the received RF signals using one or more predetermined thresholds for the waveform detection. The method further includes displaying information related to individual pulses detected from the RF pulses.

DETAILED DESCRIPTION OF THE EMBODIMENTS

Figure 1:
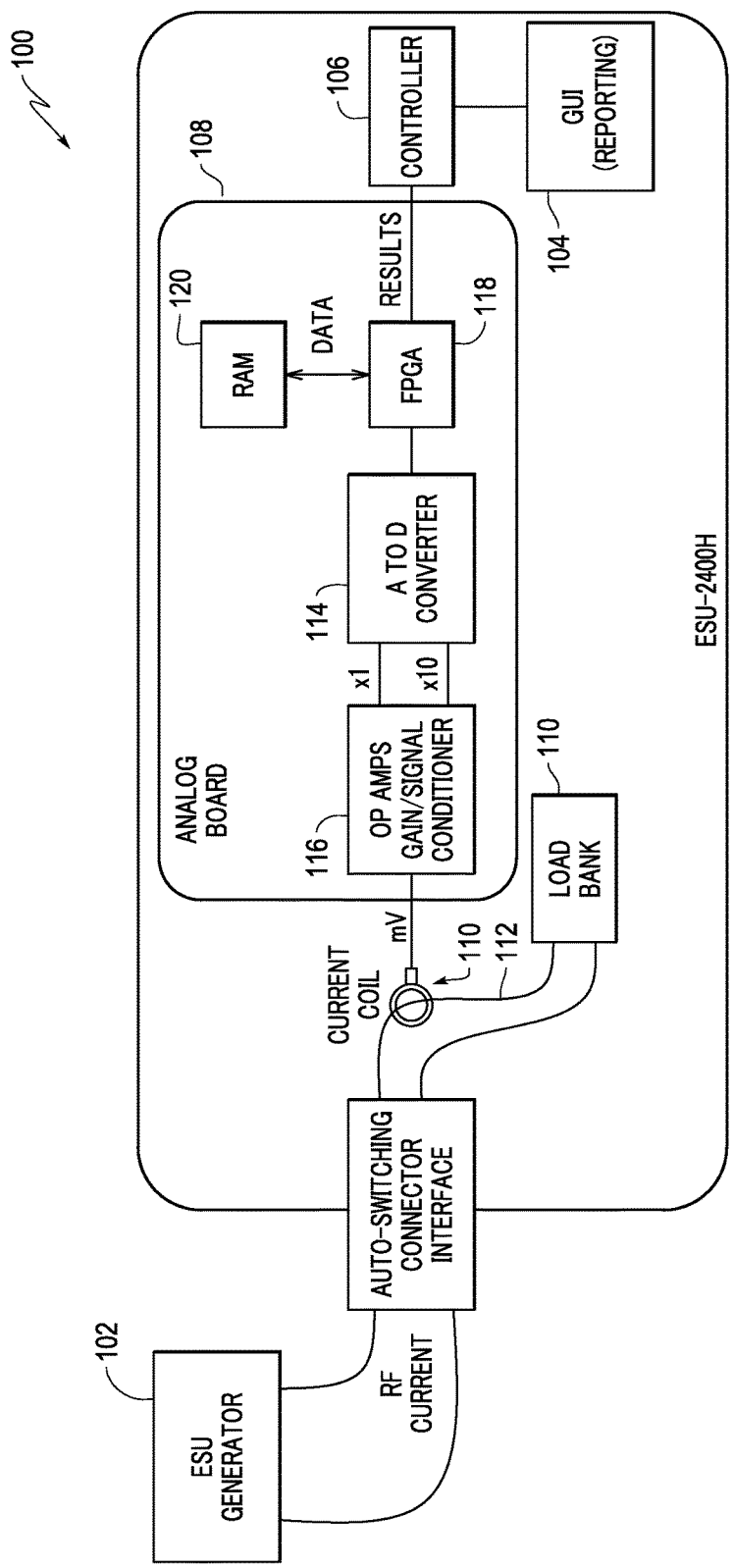
FIG. 1 is a block diagram of an electrosurgical unit analyzer in accordance with one embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry, between software elements or between hardware and software implementations. Thus, for example, one or more of the functional blocks may be implemented in a single piece of hardware or multiple pieces of hardware. Similarly, the software programs may be stand-alone programs, may be incorporated as subroutines in an operating system, may be implemented in a field-programmable gate array, and the like. It should be understood that the various embodiments are not limited to the arrangements and instrumentality shown in the drawings.

As used herein, the terms "system," "subsystem," "unit," or "module" may include any combination of hardware and/or software system that operates to perform one or more functions. For example, a system, subsystem, unit, or module may include a computer processor, controller, or other logic-based device that performs operations based on instructions stored on a tangible and non-transitory computer readable storage medium, such as a computer memory. Alternatively, a system, subsystem, unit, or module may include a hard-wired device that performs operations based on hard-wired logic of the device. The systems, subsystems, modules, or units shown in the attached figures may represent the hardware that operates based on software or hard-wired instructions, the software that directs hardware to perform the operations, or a combination thereof.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for testing medical equipment, which in some embodiments includes electrosurgical devices. The various embodiments may be used, for example, to calibrate and/or perform routine performance verification of electrosurgical devices that include electrosurgical generators. It should be noted that although various embodiments may be described in connection with testing particular electrosurgical devices, the various embodiments may be used to test different types of devices for use in various different applications. Additionally, while various embodiments may be described in connection with testing the operation of an electrosurgical device with respect to particular drive signals, such as particular waveforms, the various embodiments may be used to test different drive signals and different waveforms, which may be complex waveforms.

Various embodiments are programmable to allow for testing of different drive signals, such as different waveforms. For example, one or more embodiments may be configured to test one or more different waveforms, such as measuring and/or analyzing advanced generator outputs from an electrosurgical device, which may be pulsed RF at multiple different amplitudes (e.g., three different amplitudes). In various embodiments, pulse detection of the pulsed RF signal may be performed "on the fly".

In some embodiments, a testing device allows for measuring different basic or complex waveforms and may be programmable via a field-programmable gate array (FPGA). Using the FPGA, complex processing, including complex mathematics and analysis may be performed. In some embodiments, RMS computations as described herein may be offloaded from the CPU of the electrosurgical device, thereby allowing for more samples to be processed to provide the technical effect of a greater sample size and measurement over a longer duration.

In various embodiments, an FPGA designed electrosurgical unit analyzer is completely customizable, for example, programmed in a VHDL programming language. However, it should be appreciated that other programming languages and methods may be used as known in the art. With the programmable functionality of the electrosurgical unit analyzer device, different code may be written, for example to allow setting of multiple pulse thresholds to test complex pulsed outputs. In one or more embodiments, the electrosurgical unit analyzer device may be configured to allow for the detection of one or more thresholds (e.g., based on a user input or automatically) and allow for changing the one or more thresholds as desired or needed.

Various embodiments allow for the detection, measurement and/or analysis of one or more signals or waveforms with more accuracy or resolution than is possible with oscilloscopes. Moreover, the operations performed using an oscilloscope require manual measurements, which may result in the need for more measurement windows for detection. Various embodiments allow for an automatic configuration to be performed. For example, as described herein, an operator or user is able to set one or more thresholds and the electrosurgical unit analyzer is auto-configured to automatically perform an analysis of an input signal based on the one or more thresholds.

Figure 2:
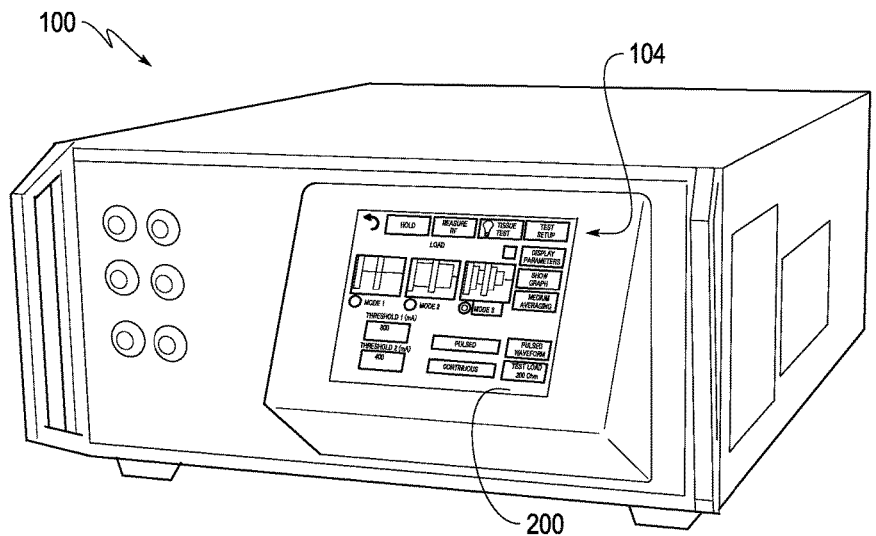
FIG. 2 is diagram of an electrosurgical unit analyzer in accordance with an embodiment.

In one embodiment, as illustrated in FIGS. 1 and 2, an electrosurgical unit analyzer 100 (also referred to as an electrosurgical unit testing device or analyzer) is provided and configured to measure the output of an electrosurgical (ESU) generator 102, which may form part of an electrosurgical device or system. The ESU generator 102 may use different waveforms that control high frequency energy to provide, for example, cutting of tissue for the medical industry. The electrosurgical unit analyzer 100 generally includes a user interface 104 (which may include a graphical user interface (GUI)), a controller 106 (e.g., a CPU or microcontroller unit), a measurement subsystem 108, which in some embodiments is configured as an analog board, and a load bank 110.

In operation, the measurement subsystem is configured to measure radio frequency (RF) current in a defined ranged (e.g., 0.01 to 10 MHz), which may be based on the ESU generator 102 to be tested. As can be seen in FIG. 1, a current transformer 110 (illustrated as a current coil) is used to generate a voltage that is directly proportional to the current that flows in a wire 112 that runs through (e.g., extends through) the center of the current transformer 110.

In the embodiment shown in FIG. 1, the electrosurgical unit analyzer 100 includes an analog to digital (A/D) converter 114 (e.g., a high speed A/D converter), which may form part of the measurement subsystem 108, to digitize the RF signal (illustrated as the RF signal from the ESU generator 102) at a rate of 64 Mega samples per second (MSPS) in one embodiment. However, it should be appreciated that different configurations of A/D converters may be used to digitize the RF signal at different desired or required rates.

In operation, by sampling the RF signal, each data point may be analyzed to provide information on the sampled waveform, such as RMS, peak, and peak to peak values. In some embodiments, the controller 106 is a CPU, such as the MC9512DT256 CPU available from Freescale. The controller 106 controls various operations, such as signaling the measurement subsystem 108 to start sampling data. The sampled data (e.g., RF measurements) is then processed as described in more detail herein to calculate measured parameters, such as RMS and peak values.

In the illustrated embodiment, the measurement subsystem 108 includes an operational amplifier 116 coupled (e.g., electrically connected) between the current transformer 110 and the A/D converter 114. In various embodiments, the measurement subsystem is configured to operate at a plurality of different voltage ranges. For example, in one embodiment, the measurement subsystem 108 is configured to operate at two input ranges, 0-100 mV and 0-1000 mV. However, it should be noted that the measurement subsystem 108 may be configured to operate at different voltage ranges, as well as at additional or fewer than two ranges.

In one embodiment, the 100 mV input is input to the operational amplifier 116 that provides a gain, such as a gain of 10 to the incoming signal so that the signal has the same input range to the A/D converter 114 as the 1000 mV range. It should be noted that in the illustrated embodiment, the A/D converter 114 is a two channel A/D converter that is connected between the operational amplifier 116 and an FPGA 118. Additionally, a memory 120 (e.g., RAM) is provided and illustrated as on-board memory in FIG. 1 (i.e., coupled to the measurement subsystem 108). The memory 120 in various embodiments is configured to store digitized A/D converter samples received through the FPGA 118.

It should be noted that the two-channel A/D converter 114 is shown as an example and a different multi-channel A/D converter 114 with more or less channels may be used. Additionally, in some embodiments, a relay or other switch may be used to switch between input signals when, for example, the number of ranges of input signals exceeds the number of channels of the A/D converter 114. In the illustrated embodiment, the A/D converter 114 is a two channel device that receives input signals from the 100 mV and 1000 mV input ranges.

In one embodiment, the memory 120 comprises 32 MB of RAM, which in operation, can store sixteen Mega samples of data from the A/D converter 114, which corresponds to 262 milliseconds (ms) of data. It should be appreciated that different sizes of memory 120 may be provided as needed, for example, based on a desired or required sample size or sample duration.

In operation, the FPGA 118 is programmed to facilitate the conversion process, which in various embodiments results in an increase in speed of the conversion process. For example, in various embodiments, the FPGA 118 may be programmed to perform high-speed functions to allow the FPGA 118 to store the A/D converter samples in the memory 120 and compute the RMS computations faster than the controller 106. It should be noted that because each sample received from the A/D converter 114 passes through the FPGA 118, the samples can be used to generate pulsed waveform signals (instead of a hardware based peak detection). Thus, for example, the FPGA based design allows for a pulsed mode threshold to be programmable in software and not fixed by the hardware.

Additionally, the programmable aspect of the FPGA 118 allows for programming different test pulses, such as for advanced pulse modes where multiple thresholds can be used to determine bursts of RF waveforms at different amplitudes. For example, various embodiments may be programmed to be compatible with outputs from different ESU generators as are known. As should be appreciated, the FPGA 118 may be programmed for other advanced waveforms for particular ESU generator manufacturers, and the FPGA 118 can be updated to include an analysis algorithm compatible with these different waveforms.

Figure 3:
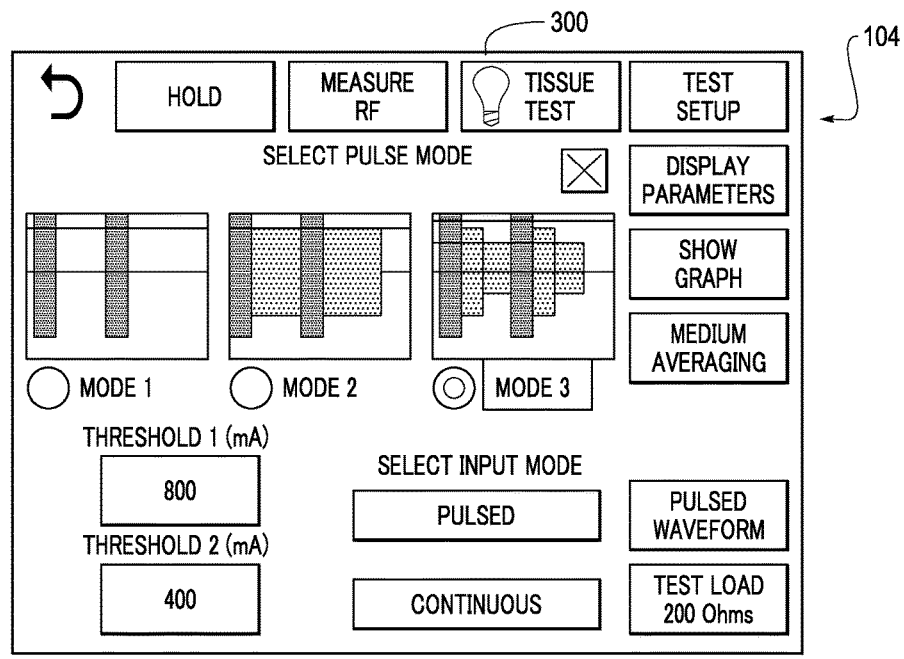
FIG. 3 is a diagram illustrating a user interface in accordance with an embodiment.

In various embodiments, the user interface 104 may be embodied as a display 200, which may be a touchscreen in some embodiments. As shown in FIG. 3, the user interface 104 may provide a control screen 300 that allows for the selection of different operating or testing criteria. For example, in the illustrated control screen 300, a pulse mode configuration may be selected. However, it should be noted that various embodiments may also allow for measurement of non-pulsed waveforms, such as continuous fixed amplitude waveforms.

Different types of waveforms that may be analyzed will now be described. However, as should be appreciated, the programmable aspects of various embodiments allows for other types of waveforms to be analyzed.

Figure 4:
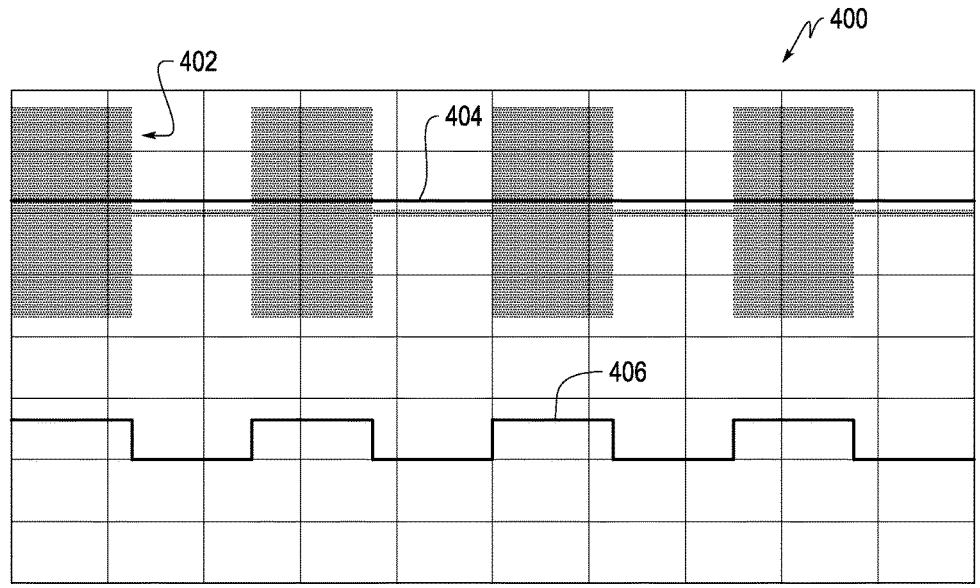
FIG. 4 is a graph illustrating waveform detection in accordance with an embodiment.

FIG. 4 is a graph 400 illustrating one embodiment of pulsed waveform detection. In the graph 400, the horizontal axis corresponds to time and the vertical amplitude corresponds to magnitude. As can be seen by the waveform 402, the RF output from the generator (e.g., the ESU generator 102 shown in FIG. 1) is turned on and off at regular intervals illustrated by the square wave waveform 402 that has a fixed amplitude.

Figure 5:
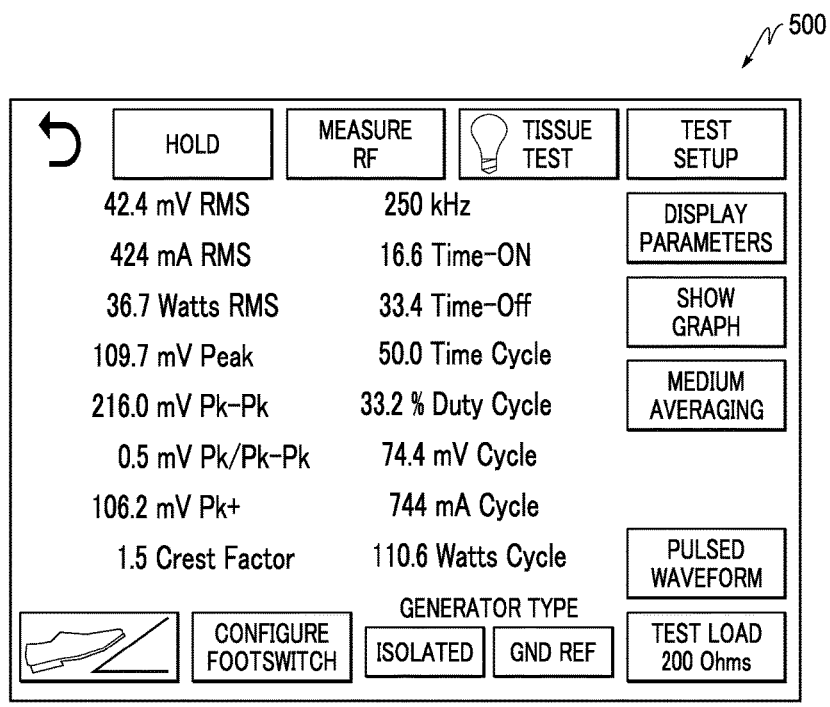
FIG. 5 is a diagram illustrating measurement information determined in accordance with various embodiments and corresponding to the waveform of FIG. 4.

In various embodiments, the electrosurgical unit analyzer 100 uses the FPGA 118 to provide a pulse detection circuit that can detect the presence of the RF signal and can calculate the RMS output of the overall waveform, as well as the individual pulses of the RF output. For example, the FPGA 118 is programmed to operate as a peak detector having a fixed threshold to provide pulse detection for the waveform 402 having the fixed threshold voltage. In operation, when the input signal is over a defined threshold (e.g., a predetermined threshold) illustrated by the line 404, the input is considered to be present, which is illustrated as the signal 406 (Pulse Detect) with the corresponding measurements 500 shown in FIG. 5. As can be seen, pulse detection is provided allowing for measurement results showing additional information and not just an averaged output.

It should be appreciated that the measurements 500 may be displayed as part of the user interface 104.

Figure 6:
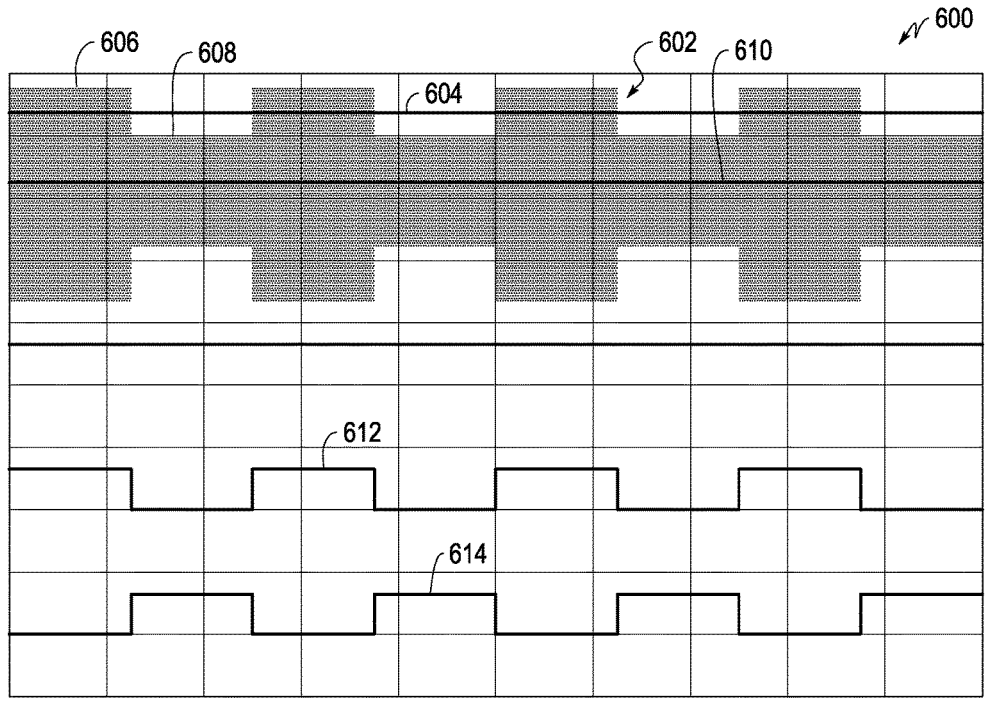
FIG. 6 is a graph illustrating waveform detection in accordance with another embodiment.

Various embodiments also provide pulse detection of waveforms that have the RF signal continuously on, but at different amplitudes by programming different thresholds. Thus, the various embodiments are not limited to a single fixed threshold. For example, as shown in FIG. 6, various embodiments can measure waveform pulses of a waveform 602 having different amplitudes by programming the FPGA 118 to operate as a pulse detection circuit operating at multiple thresholds. For example, the line 404 represents a programmable threshold (e.g., programmable threshold magnitude value) that allows for the detection of the two segments or pulses 606 and 608 of RF energy. The line 610 represents a fixed threshold that is not programmable in contrast to the programmable threshold of various embodiments. As can be seen, because the amplitude of the RF waveform 602 is always above the line 610, if a single fixed threshold were used, measurement of each segment 606 and 608 of the RF waveform could not be provided. Instead, the system would report a continuously "on" condition.

Figure 7:
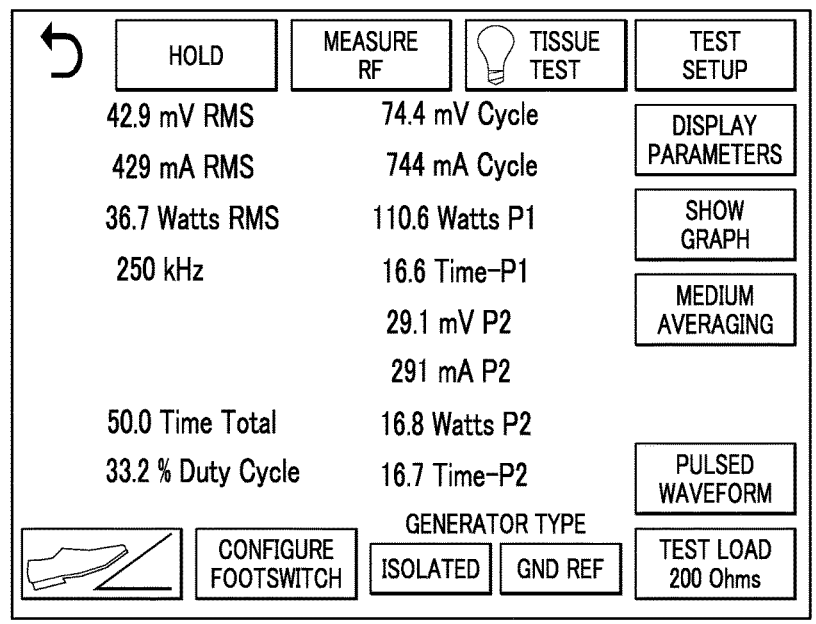
FIG. 7 is a diagram illustrating measurement information determined in accordance with various embodiments and corresponding to the waveform of FIG. 6.

In various embodiments, the electrosurgical unit analyzer 100 uses the FPGA 118 to provide a pulse detection circuit that can detect the presence of the RF signal having a varying magnitude and can calculate the RMS output of the overall waveform, as well as the individual pulses 606 and 608 of the RF output. For example, the FPGA 118 is programmed to operate as a peak detector having an adjustable threshold (which may be dynamically adjusted) to provide pulse detection for the waveform 602 having a varying magnitude. In operation, the threshold is programmed to a value that allows for distinguishing between the pulses 606 and 608. In the illustrated embodiment, when the input signal exceeds the defined threshold (e.g., a predetermined threshold) illustrated by the line 610, the pulse 606 is considered to be present, which is illustrated as the signal 612 (Pulse 1 Detect) with the corresponding measurements 700 shown in FIG. 7. Additionally, in the illustrated embodiment, when the input signal is below the defined threshold (e.g., a predetermined threshold) illustrated by the line 610, the pulse 608 is considered to be present, which is illustrated as the signal 614 (Pulse 2 Detect) with the corresponding measurements 700 shown in FIG. 7. In some testing application, such as for hospital equipment where measurements are important or critical, the waveforms can become very complex or complicated. Unlike conventional testing equipment or conventional testing applications, various embodiments provide measurements that are understandable and that can be confidently relied upon by the operator or user. For example, a user of one or more embodiments described herein will be provided with numerical outputs that can be used to confirm OEM specification unlike conventional testing equipment or conventional testing applications, which may output numbers that are not accurate or which the operator or user does not understand or know what the numbers mean.

As can be seen, pulse detection is provided allowing for measurement results showing additional information and not just an averaged output. It should be appreciated that the measurements 700 may be displayed as part of the user interface 104. As a result, when a user is testing, for example for OEM specifications, to verify the proper operation of the device under test, various embodiments allow for performing manufacturer testing, which may include very specific requirements, with a minimal amount of input from the user and providing consistent results that can be compared over time, with particular OEM requirements, or for different devices to be tested.

Unlike an oscilloscope, wherein aliasing can occur, resulting in missing data because the sample rate is too slow, various embodiments allow for fixing the sample rate to ensure that the signal is properly detected and analyzed. For example, in one or more embodiments, the same rate may be set based on and to pick up the "worst case" signal. In some embodiments, various embodiments sense or identify a "dead period" and ignore any data during this period of time. Various embodiments are able to sense this "dead period" because the sample time is long enough and acquires enough data to analyze the data to determine these periods, which is not possible with oscilloscopes or other testing systems.

For example, in operation, in various embodiments, an analysis of the signal is started when the signal crosses a threshold as described herein. It should be noted that various embodiments are constantly or continually monitoring the signal for a threshold crossing once monitoring is started. In some embodiments, for example, if after a predetermined amount of data (e.g., 32 megabytes) is monitored and there is no detection of a crossing of the threshold value, the data that has been acquired is deleted. In some embodiments, detection is triggered off of a single edge of the input signal. However, different trigger events may be used.

Figure 8:
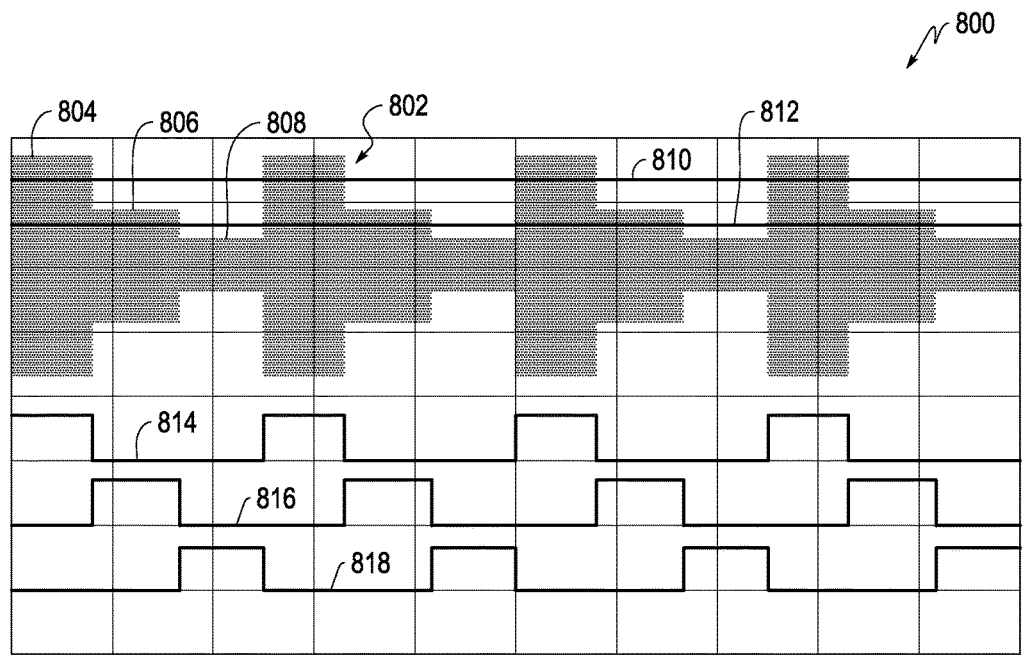
FIG. 8 is a graph illustrating waveform detection in accordance with another embodiment.
Figure 9:
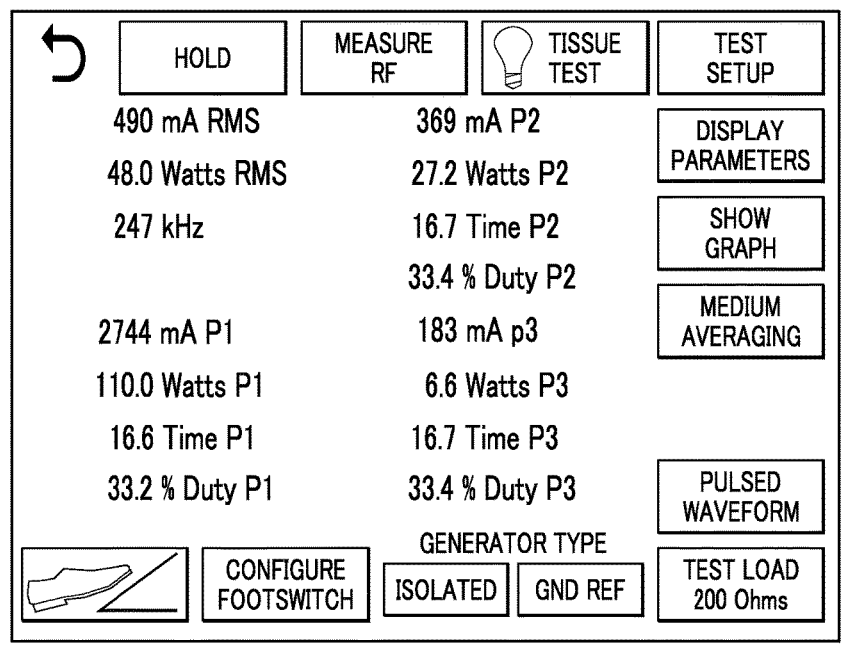
FIG. 9 is a diagram illustrating measurement information determined in accordance with various embodiments and corresponding to the waveform of FIG. 8.

The programmable FPGA 118 also allows for multiple thresholds to be defined to detect output sets of pulses at different amplitudes. For example, as shown in FIG. 8, using two thresholds, it is possible to detect three different amplitudes of an RF waveform 802, which allows for reporting on individual pulse segments as shown in FIG. 9. Thus, in this embodiment, complex pulse analysis may be provided for analysis and maintenance of ESU generators.

Thus, in some embodiments, the electrosurgical unit analyzer 100 uses the FPGA 118 to provide a pulse detection circuit that can detect the presence of the RF signal having a varying magnitude and can calculate the RMS output of the overall waveform, as well as the individual pulses of the RF output using multiple threshold. For example, in this embodiment, the FPGA 118 is programmed to operate as a peak detector having an adjustable threshold (which may be dynamically adjusted) to provide pulse detection for the waveform 802 having a varying magnitude. In operation, the thresholds are programmed to values that allow for distinguishing between the pulses 804, 806 and 808. In the illustrated embodiment, when the input signal exceeds the defined thresholds (e.g., predetermined thresholds) illustrated by the lines 810 and 812, the pulse 804 is considered to be present, which is illustrated as the signal 814 (Pulse 1 Detect) with the corresponding measurements 900 shown in FIG. 9. Additionally, in the illustrated embodiment, when the input signal is below the defined threshold (e.g., a predetermined threshold) illustrated by the line 810, but above the threshold illustrated by the line 812, the pulse 806 is considered to be present, which is illustrated as the signal 816 (Pulse 2 Detect) with the corresponding measurements 900 shown in FIG. 9. Further, in the illustrated embodiment, when the input signal is below the defined thresholds (e.g., predetermined thresholds) illustrated by the lines 810 and 812, the pulse 808 is considered to be present, which is illustrated as the signal 818 (Pulse 3 Detect) with the corresponding measurements 900 shown in FIG. 9.

As can be seen, pulse detection is provided allowing for measurement results showing additional information and not just an averaged output. It should be appreciated that the measurements 900 may be displayed as part of the user interface 104.

Figure 10:
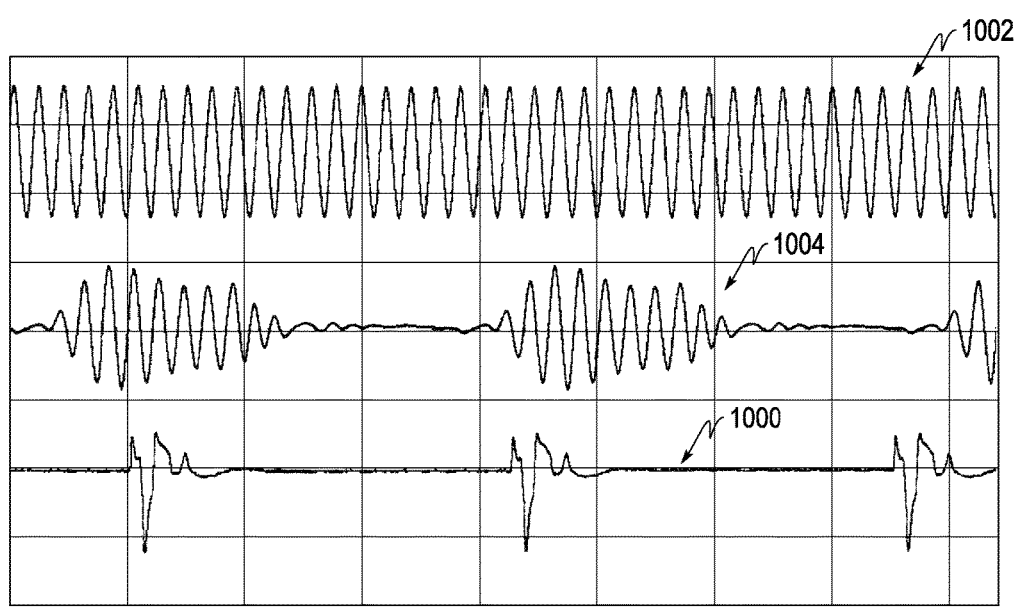
FIG. 10 is a graph illustrating different types of waveforms that may be detected and analyzed in accordance with various embodiments.

Variations and modifications are contemplated. For example, one or more embodiments may be configured to provide frequency measurements, such as for different continuous sinusoidal waveforms such as illustrated in FIG. 10. FIG. 10 illustrates the difference between a continuous waveform 1002 and non-continuous waveforms 1004 and 1006 that may be detected using one or more embodiments. Moreover, the programmable FPGA 118 may be configured to implement custom algorithms that can analyze a non-continuous waveform and calculate frequency.

Thus, various embodiments provide an electrosurgical unit analyzer 100 having a programmable design that allows for the detection of different types of waveforms. For example, various embodiments allow for the measurement of advanced or complex generator outputs with pulsed RF having multiple amplitudes, which may be continuous or pulsed waveforms. Additionally, the programmable aspects allow for user selected measurement parameters and definable screens. The electrosurgical unit analyzer 100 can be programmed to use and change the threshold detection.

It should be noted that the various components of the electrosurgical unit analyzer 100 may be modified as desired or needed. For example, the load bank 110 may be changed. In some embodiments, for example, the load bank 100 allows for test loads from 0 ohms to 6400 ohms in 1 ohm increments. However, other load values may be provided.

In some embodiments, high voltage setup relays may be provided to control the measurement path. These relays allow the user to switch between power measurements, leakage measurements, REM/ARM/CQM testing, as well as run an auto-sequence including multiple tests.

For example, one or more embodiments provide for an auto-sequencing procedure that automatically performs a predetermined set of steps for testing a device. In one embodiment, the sequence of steps for testing the device includes initiates a testing procedure, performs a setup based on the device to be tested, runs one or more tests (using thresholds as described herein), analyzes the test results, and generates a pass/fail output for each of the tests. Thus, a user may be presented with a displayed or printed output that is simple to understand.

Figure 11:
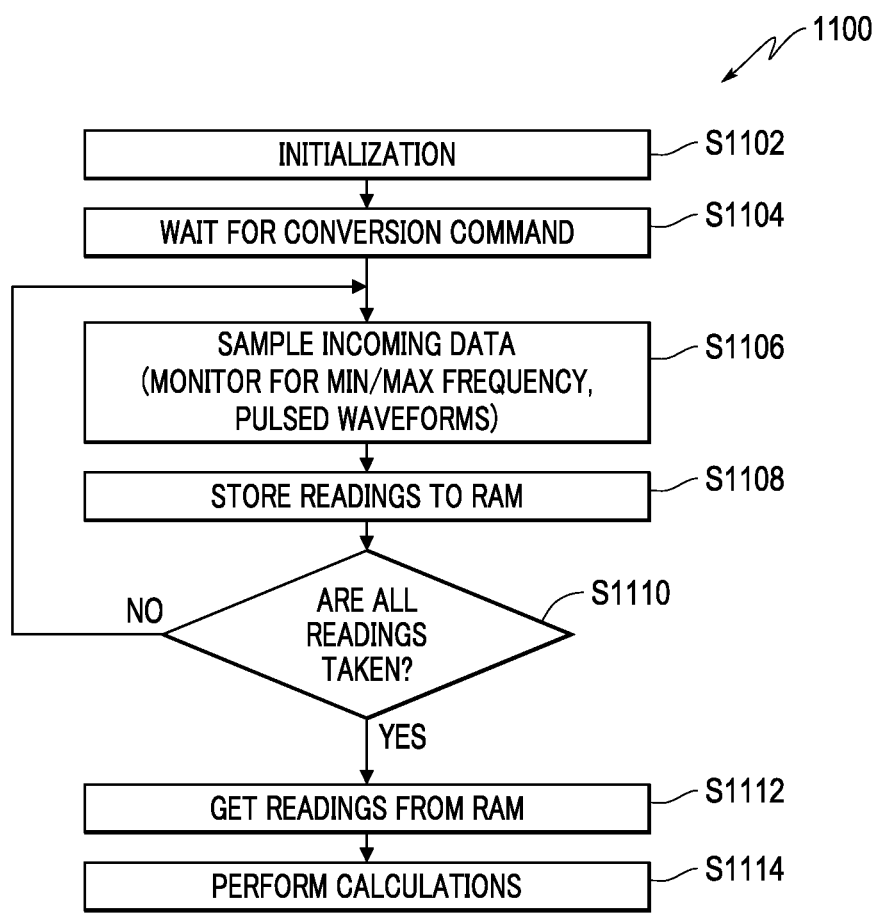
FIG. 11 is a flowchart of a method of a method in accordance with various embodiments.

Various embodiments provide a method 1100 as shown in FIG. 11. The method 1100 may be implemented by one or more of the systems described herein. The steps of the method 1100 may be performed in a different order than shown and the steps may be repeated or removed. Additionally, one or more steps may be performed sequentially, concurrently or simultaneously. In some embodiments, the method 1100 may be used as an RMS conversion process that the FPGA 118 (shown in FIG. 1) performs.

The method 1100 includes an initialization process at 1102. For example, after a start up routine and self-check is performed to ensure that the electrosurgical unit analyzer 100 (shown in FIG. 1) is operating properly, the analyzer is initialized such that one or more thresholds are defined as described herein. The method 1100 includes waiting for a conversion command at 1104, which starts a monitoring process as described in herein.

At 1106 of the method 1100, incoming data is sampled. For example, incoming test data is monitored for maximum and minimum values, frequency and pulsed waveform characteristics, among others. The acquired data, such as measurements or readings are stored at 1108, for example, to the RAM 120 (shown in FIG. 1). The process of sampling at 1106 and storing readings at 1108 is repeated (loop) until all necessary or desired readings are acquired at 1110. For example, based on the characteristics of the signal to be tested or the particular testing requirements, the loop is performed to acquired data sufficient to perform analysis as described herein.

The stored readings (e.g., monitored or measured data) is obtained from the RAM at 1112, which is then used to perform calculations at 1114. For example, the stored data may be processed as described herein to determine RMS or other values.

It should be noted that the various embodiments may be implemented in hardware, software or a combination thereof. The various embodiments and/or components, for example, the modules, or components and controllers therein, also may be implemented as part of one or more computers or processors or FPGAs. The computer or processor or FPGA may include a computing device, an input device, a display unit and an interface, for example, for accessing the Internet. The computer or processor may include a microprocessor. The microprocessor may be connected to a communication bus. The computer or processor or FPGA may also include a memory. The memory may include Random Access Memory (RAM) and Read Only Memory (ROM). The computer or processor or FPGA further may include a storage device, which may be a hard disk drive or a removable storage drive such as a floppy disk drive, optical disk drive, and the like. The storage device may also be other similar means for loading computer programs or other instructions into the computer or processor.

As used herein, the terms "system," "circuit," "component," or "module" may include a hardware and/or software system that operates to perform one or more functions. For example, a module, circuit, component, or system may include a computer processor, controller, or other logic-based device that performs operations based on instructions stored on a tangible and non-transitory computer readable storage medium, such as a computer memory. Alternatively, a module, circuit, component, or system may include a hard-wired device that performs operations based on hard-wired logic of the device. The modules or circuits or components shown in the attached figures may represent the hardware that operates based on software or hard-wired instructions, the software that directs hardware to perform the operations, or a combination thereof.

The block diagrams of embodiments herein illustrate various blocks labeled "circuit" or "module." It is to be understood that the circuits or modules may be implemented as hardware with associated instructions (e.g., software stored on a tangible and non-transitory computer readable storage medium, such as a computer hard drive, ROM, RAM, or the like) that perform the operations described herein. The hardware may include state machine circuitry hard-wired to perform the functions described herein. Optionally, the hardware may include electronic circuits that include and/or are connected to one or more logic-based devices, such as microprocessors, processors, controllers, or the like. Optionally, the modules may represent processing circuitry such as one or more field programmable gate array (FPGA), application specific integrated circuit (ASIC), or microprocessor. The circuit modules in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) paragraph, unless and until such claim limitations expressly use the phrase "means for" followed by a statement of function void of further structure.

What is claimed is:

1. An electrosurgical unit analyzer comprising:
an input configured to receive radio frequency (RF) signals from an electrosurgical generator;
a measurement subsystem configured for programmable waveform detection corresponding to the received RF signals, the measurement subsystem including a field-programmable gate array (FPGA) defining one or more thresholds for the waveform detection;
an analog to digital (A/D) converter coupled to the FPGA; and
a user interface displaying information relating to individual pulses detected from the RF signals.

2. The electrosurgical unit analyzer of claim 1, wherein the measurement subsystem is configured as an analog board having on-board memory.

3. The electrosurgical unit analyzer of claim 2, wherein the on-board memory comprises at least 32 megabytes of RAM.

4. The electrosurgical unit analyzer of claim 1, further comprising an operational amplifier coupling the measurement subsystem to a current transformer.

5. An electrosurgical unit analyzer comprising:
an input configured to receive radio frequency (RF) signals from an electrosurgical generator;
a measurement subsystem configured for programmable waveform detection corresponding to the received RF signals, the measurement subsystem including a field-programmable gate array (FPGA) defining one or more thresholds for the waveform detection, wherein the FPGA is programmable to define plural thresholds for waveform detection; and
a user interface displaying information relating to individual pulses detected from the RF signals.

6. The electrosurgical unit analyzer of claim 5, wherein the plural thresholds define waveform magnitudes to distinguish between different segments or pulses of the waveform.

7. The electrosurgical unit analyzer of claim 1, wherein the measurement subsystem is configured to perform an auto-sequencing process to test the electrosurgical generator.

8. The electrosurgical unit analyzer of claim 1, wherein the measurement subsystem is configured to identify a dead period and ignore data acquired during the dead period corresponding to the RF signal.

9. The electrosurgical unit analyzer of claim 1, wherein the measurement subsystem is configured to determine a pass/fail result for each of a plurality of measurements and the user interface is configured to display the pass/fail results.

10. A method for analyzing radio frequency (RF) signals from an electrosurgical generator, the method comprising:
acquiring as an input, RF signal from the electrosurgical generator;
performing waveform detection on the received RF signals using one or more predetermined thresholds for the waveform detection;
configuring a field-programmable gate array (FPGA) to receive an input to define the one or more predetermined thresholds for the waveform detection;
performing analog to digital (A/D) conversion of an output from the FPGA; and
displaying information related to individual pulses detected from the RF pulses.

11. The method of claim 10, further comprising acquiring at least 32 megabytes of data for the input RF signal.

12. The method of claim 10, further comprising defining plural thresholds for waveform detection.

13. The method of claim 12, further comprising defining the plural thresholds to define waveform magnitudes to distinguish between different segments or pulses of the waveform.

14. The method of claim 10, further comprising performing an auto-sequencing process to test the electrosurgical generator.

15. The method of claim 10, further comprising identifying a dead period and ignoring data acquired during the dead period corresponding to the RF signal.

16. The method of claim 10, further comprising determining a pass/fail result for each of a plurality of measurements and displaying the pass/fail results.

17. A non-transitory computer readable medium having instruction thereon to instruct a processor to:
acquire as an input, RF signal from the electrosurgical generator;
perform waveform detection on the received RF signals using one more predetermined thresholds for the waveform detection;
configure a field-programmable gate array (FPGA) to receive an input to define the one or more predetermined thresholds for the waveform detection;
perform analog to digital (A/D) conversion of an output from the FPGA; and
display information related to individual pulses detected from the RF pulses.

* * * * *